United States Patent [19]

Mohacsi

[11] 4,374,139
[45] Feb. 15, 1983

[54] LEVOROTATORY N-SUBSTITUTED ACYLMORPHINANS USEFUL AS ANALGESIC AGENTS

[75] Inventor: Ernest Mohacsi, Nutley, N.J.

[73] Assignee: Hoffmann-La Roche Inc., Nutley, N.J.

[21] Appl. No.: 319,482

[22] Filed: Nov. 9, 1981

[51] Int. Cl.³ ............... A61K 31/485; C07D 221/28
[52] U.S. Cl. .................................... 424/260; 546/74
[58] Field of Search ......................... 546/74; 424/260

[56] References Cited

U.S. PATENT DOCUMENTS 3,723,437   3/1973   Wiesner ............................. 546/74
3,914,233  10/1975   Mohacsi et al. ................... 546/74

OTHER PUBLICATIONS

Belanger, et al., J. Org. Chem., vol. 43, No. 5, pp. 906–909 (1978).

Primary Examiner—Donald G. Daus
Assistant Examiner—Diana G. Rivers
Attorney, Agent, or Firm—Jon S. Saxe; Bernard S. Leon; William G. Isgro

[57] ABSTRACT

Levorotatory N-substituted acylmorphinans of the formula

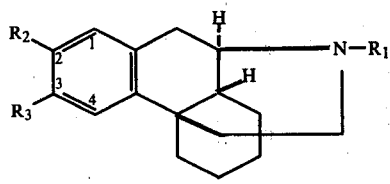

wherein $R_1$ is hydrogen, lower alkyl, lower alkenyl, cycloalkyl-lower alkyl, cyano-lower alkyl, aryl-lower alkyl, or 5- or 6-membered heterocyclic-lower alkyl, and one of $R_2$ or $R_3$ is hydrogen and the other of $R_2$ or $R_3$ is alkanoyl of 2 to 7 carbon atoms, aroyl, trifluoromethylcarbonyl or

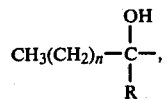

wherein R is hydrogen or lower alkyl and n is an integer of 0 to 6, and salts thereof with pharmaceutically acceptable acid addition salts, are described. The compounds of formula I are useful as analgesic agents.

22 Claims, No Drawings

LEVOROTATORY N-SUBSTITUTED ACYLMORPHINANS USEFUL AS ANALGESIC AGENTS

BRIEF SUMMARY OF THE INVENTION

The invention relates to compounds of the formula wherein $R_1$ is hydrogen, lower alkyl, lower alkenyl, cycloalkyl-lower alkyl, cyano-lower alkyl, aryl-lower alkyl, 5- or 6-membered heterocyclic-lower alkyl, and one of $R_2$ or $R_3$ is hydrogen and the other of $R_2$ or $R_3$ is alkanoyl of 2 to 7 carbon atoms, aroyl, trifluoromethylcarbonyl or $$CH_3(CH_2)_n - \underset{R}{\overset{OH}{\underset{|}{\overset{|}{C}}}} -,$$

wherein R is hydrogen or lower alkyl and n is an integer of 0 to 6, and salts thereof with pharmaceutically acceptable acid addition salts, which are useful as analgesic agents.

DETAILED DESCRIPTION OF THE INVENTION

The term "lower alkyl" includes both straight and branched chain saturated aliphatic hydrocarbon groups containing from 1 to 7 carbon atoms, i.e., methyl, ethyl, n-propyl, isopropyl, n-butyl, isobutyl, and the like, with methyl being preferred. The term "lower alkenyl" designates both straight and branched chain aliphatic hydrocarbon groups containing from 2 to 7 carbon atoms which contain one olefinic double bond such as vinyl, allyl, prop-2-en-1-yl and the like. The preferred lower alkenyl groups are $$-CH_2-CH=CH_2, -CH_2-CH=\underset{|}{\overset{CH_3}{C}}-CH_3 \text{ and}$$

$$-CH_2-\underset{|}{\overset{CH_3}{C}}=CH_2.$$

The term "cyclo-lower alkyl" designates saturated cyclic aliphatic hydrocarbon groups containing a ring of from 3 to 6 carbon atoms. Among the preferred cyclo-lower alkyl groups are cyclopropyl, cyclobutyl and cyclohexyl. The term "alkanoyl", designates a radical derived from an aliphatic carboxylic acid of 2 to 7 carbon atoms. Among the preferred alkanoyl groups are acetyl and the like.

The term "aroyl" designates a radical derived from an aromatic carboxylic acid. Among the preferred aroyl groups are benzoyl, naphthoyl and the like.

The term "heterocyclic" designates hydrocarbon ring systems containing a hetero atom selected from the group consisting of oxygen, nitrogen, or sulfur and having 5 or 6 members in the ring structure. Among the preferred heterocyclic ring structures are thienyl, pyrrolyl, furyl, pyridyl, pyranyl and the like.

The term "aromatic" or "aryl" designates hydrocarbon ring systems, such as, phenyl, naphthyl with phenyl being preferred.

The invention relates to compounds of the formula wherein $R_1$ is hydrogen, lower alkyl, lower alkenyl, cycloalkyl-lower alkyl, cyano-lower alkyl, aryl-lower alkyl, or 5- or 6-membered heterocyclic-lower alkyl, and one of $R_2$ or $R_3$ is hydrogen and the other of $R_2$ or $R_3$ is alkanoyl of 2 to 7 carbon atoms, aroyl, trifluoromethylcarbonyl or $$CH_3(CH_2)_n - \underset{R}{\overset{OH}{\underset{|}{\overset{|}{C}}}} -,$$

wherein R is hydrogen or lower alkyl and n is an integer of 0 to 6, and salts thereof with pharmaceutically acceptable acid addition salts.

A preferred subgroup comprises compounds of formula I wherein $R_1$ is cycloalkyl-lower alkyl, $R_2$ is hydrogen and $R_3$ is alkanoyl of 2 to 7 carbon atoms.

Another preferred subgroup comprises compounds of formula I wherein $R_1$ is lower alkyl, $R_2$ is hydrogen and $R_3$ is alkanoyl of 2 to 7 carbon atoms.

Yet another preferred subgroup comprises compounds of formula I wherein $R_1$ is lower alkenyl, $R_2$ is hydrogen and $R_3$ is alkanoyl of 2 to 7 carbon atoms.

A further preferred subgroup comprises compounds of formula I wherein $R_1$ is phenyl-lower alkyl, $R_2$ is hydrogen and $R_3$ is alkanoyl of 2 to 7 carbon atoms.

Still another preferred subgroup comprises compounds of formula I wherein $R_1$ is lower alkyl, $R_2$ is hydrogen and $R_3$ is $$CH_3(CH_2)_n - \underset{R}{\overset{OH}{\underset{|}{\overset{|}{C}}}} -,$$

wherein R and n are as previously described.

A preferred compound of the invention is: (−)-1-[N-(cyclopropylmethyl)morphinan-3-yl]-ethanone hydrochloride.

The compounds of the invention can be prepared as hereinafter described and illustrated by Reaction Schemes I-IV.

Reaction Scheme I

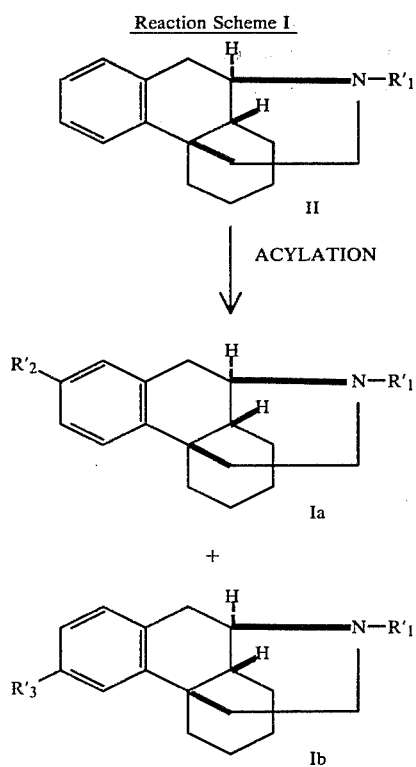

wherein $R_1'$ is lower alkyl, and $R_2'$ or $R_3'$ is hydrogen and the other of $R_2'$ or $R_3'$ is alkanoyl of 2 to 7 carbon atoms, aroyl or trifluoromethylcarbonyl.

In accordance with Reaction Scheme I, a compound of formula II, known compounds, is reacted with an acylating agents such as an acid halide, an acid anhydride or a carboxylic acid under the conditions of a Friedel-Crafts reaction. Exemplary of such acylating agents are compounds of the formulas

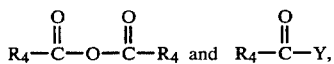

wherein $R_4$ is lower alkyl of 1 to 6 carbon atoms, aryl or trifluoromethyl, and Y is halogen or hydroxy. The acylation can be carried out with or without solvent. Exemplary of the solvents that can utilized are 1,2-dichloromethane, nitrobenzene, nitromethane, methylene chloride, carbon disulfide and the like. Exemplary of the Lewis acids that can be utilized in the Friedel-Crafts reaction are aluminum chloride, antimony pentachloride, ferric chloride, boron trifluoride, stannic chloride, antimony trichloride, aluminum bromide, boron trichloride, titanium chloride, zinc chloride and the like.

The acylation of an aromatic system by the Friedel-Crafts reaction are usually effected either with an acid chloride or an anhydride in the presence of a Lewis acid such as aluminum chloride, boron trifluoride, stannic chloride, zinc chloride, ferric chloride and the like, or with a carboxylic acid in the presence of an acid such as hydrogen fluoride, sulfuric acid, phosphoric or polyphosphoric acid. The Lewis acid catalysts are usually used in solvents such as 1,2-dichloroethane, carbon disulfide, methylene chloride, nitromethane, nitrobenzene or an excess of the hydrocarbon being acylated. The acylation reaction is usually carried out at a temperature in the range of from 0° to the boiling point of the solvent.

The reaction products which are characterized by formulas Ia and Ib can be isolated according to known procedures, such as, chromatography, crystallization and the like.

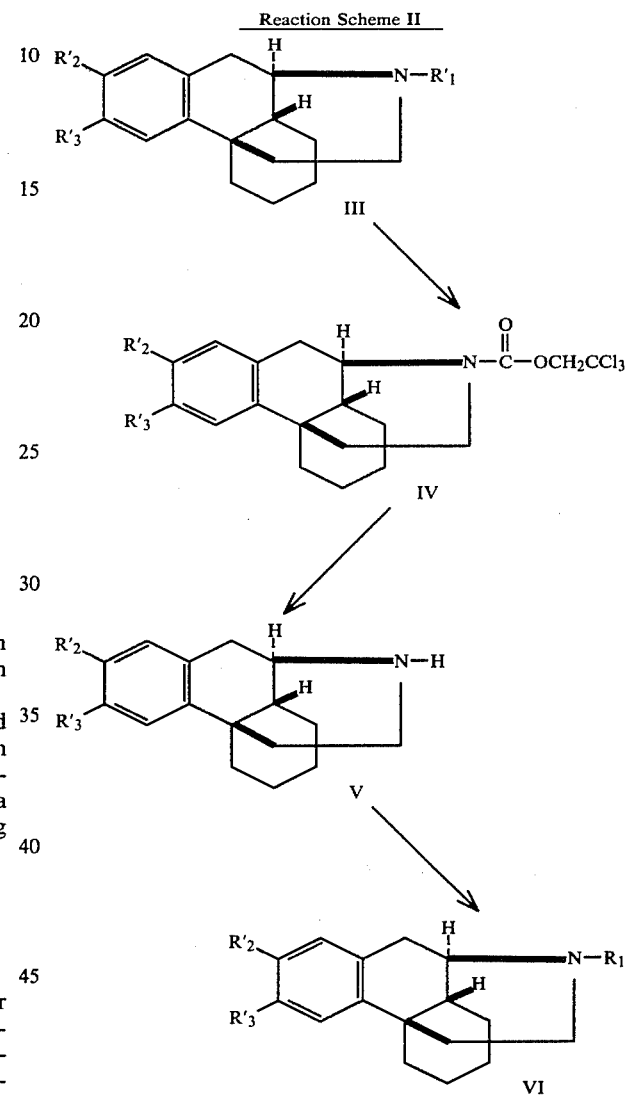

wherein $R_1$, $R_1'$, $R_2'$ and $R_3'$ are as previously described.

In accordance with Reaction Scheme II, a compound of formula III is converted to a compound of formula IV by treating the former with trichloroethyl chloroformate in an inert solvent such as benzene, toluene or the like, preferably at the reflux temperature of the reaction mixture. The compound of formula IV is converted to the compound of formula V by treatment with zinc in a lower alkanoic acid, such as acetic acid, propionic acid or the like, at room temperature and atomspheric pressure.

The compounds of formula III can be dealkylated according to known methods. Any conventional dealkylating agent can be used. Thus, cyanogen bromide followed by treatment with an inorganic acid, or phenyl or ethyl chloroformates followed by treatment with an alkali metal hydroxide in a lower alkanol can be utilized for the dealkylation.

A compound of formula V can be converted to a compound of formula VI with an alkylating agent. Exemplary of such agents are compounds of the formula $R_1X$ wherein X is halogen and $R_1$ is lower alkyl, lower alkenyl, cycloalkyl-lower alkyl, cyano-lower alkyl, phenyl-lower alkyl, or 5- or 6-membered heterocyclic-lower alkyl. Preferred solvents for the alkylation comprise dimethyl sulfoxide, dimethyl formamide or the like. The reaction is carried out in the presence of an inorganic alkali metal base such as sodium or potassium carbonate or bicarbomate at a temperature in the range of room temperature to the reflux temperature; preferably at the reflux temperature.

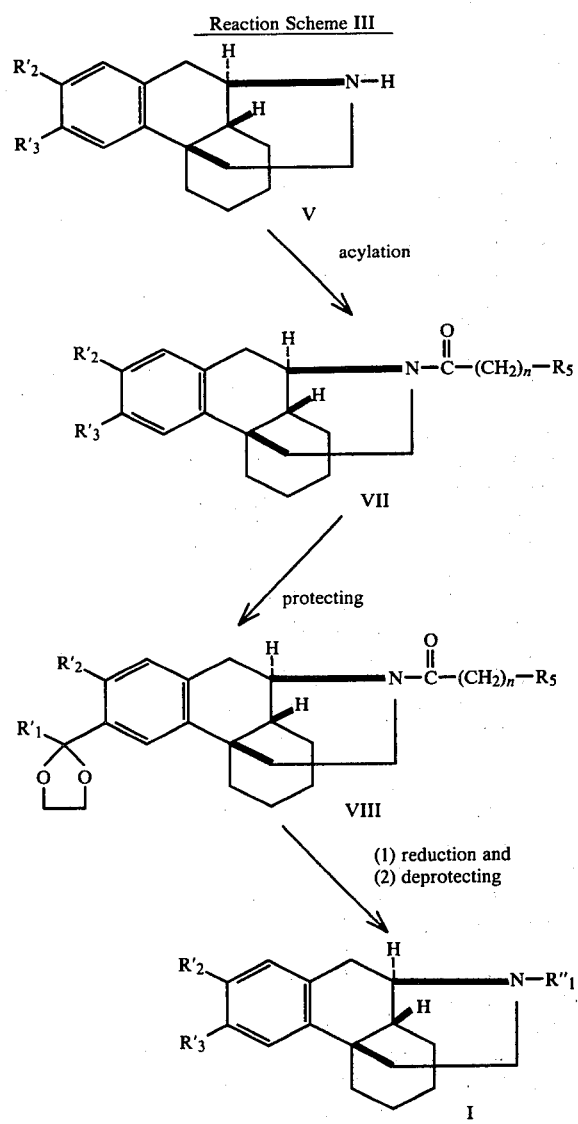

wherein $R_1'$, $R_2'$ and $R_3'$ are as previously described, $R_5$ is hydrogen, cycloalkyl, aryl or 5- or 6-membered heterocyclic, $R_1''$ is alkyl, cycloalkyl-lower alkyl, aryl-lower alkyl or 5- or 6-membered heterocyclic-lower alkyl, and n is 0 to 6.

In accordance with Reaction Scheme III, a compound of formula V is acylated with an acylating agent of the formula

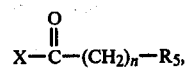

wherein X is halogen, n is an integer of 0 to 6, and $R_5$ is hydrogen, cycloalkyl, aryl or 5- or 6-membered heterocyclic in the presence of an inert organic solvent such as benzene, toluene, methylene chloride, in the presence of an organic base such as pyridine, triethylamine, or the like, at room temperature or at the boiling point of the solvent. Exemplary of the acylating agent which can be utilized are cyclopropylcarbonyl chloride, cyclobutylcarbonyl chloride, phenylacetyl chloride, furylacetyl chloride or the like.

The alkanoyl group of a compound of formula VII is protected in the form of a cyclic ketal. The most common method to form ketals from ketones comprises the reaction of the carbonyl compound with, for example, an alkane diol in the presence of an acid catalyst and the azeotropic removal of the water formed by a refluxing solvent immiscible with water. Any alkane diol such as ethylene glycol, propylene glycol and the like can be used. Solvents which can be used including benzene, toluene, xylene and the like. As the acid catalyst, one can use p-toluenesulfonic acid and the like.

The reduction and removal of the protecting group of a compound of formula VIII to a compound of formula I is effected as follows. The reduction of the amide group to the corresponding amine group is carried out with an alkali metal aluminum hydride, such as, lithium aluminum hydride and the like, utilizing known reaction conditions. For example, in the presence of a solvent such as ether, tetrahydrofuran, 1,2-dimethoxyethane, diglyme or the like, at room temperature or at reflux. Upon treatment of the resulting protected amine compound with a mineral acid, such as, hydrochloric acid, hydrobromic acid, sulfuric acid or the like, the ketal group reverts to the carbonyl compound, that is, a compound of formula I.

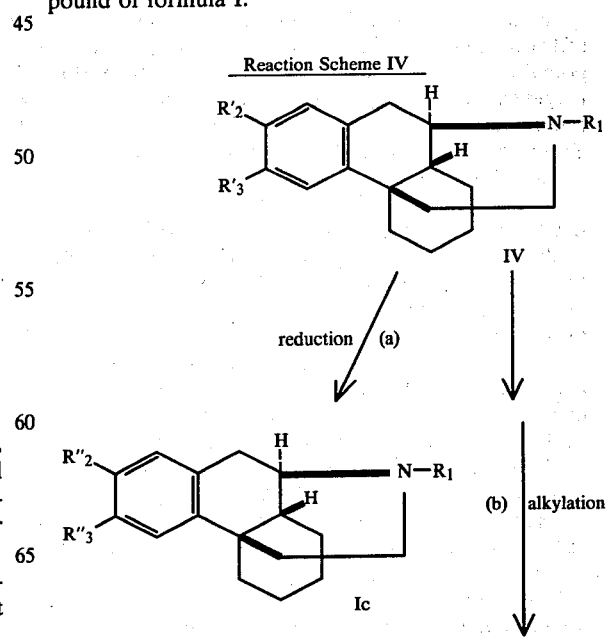

-continued
Reaction Scheme IV

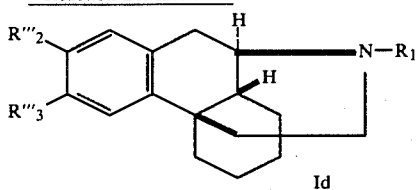

wherein one of $R_2'$ or $R_3'$ is hydrogen and the other of $R_2'$ or $R_3'$ is alkanoyl of 2 to 7 carbon atoms, aroyl or trifluoromethylcarbonyl, one of $R_2''$ or $R_3''$ is hydrogen and the other of $R_2''$ or $R_3''$ is

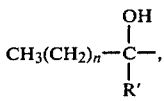

wherein $R'$ is hydrogen and n is 0 to 6, one of $R_2'''$ or $R_3'''$ is hydrogen and the other of $R_2'''$ or $R_3'''$ is

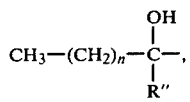

wherein $R''$ is lower alkyl and n is 0 to 6, and $R_1$ is as previously described.

In accordance with Reaction Scheme IV, in reaction step (a) a compound of formula VI is converted to a compound of formula Ic utilizing a reducing agent, such as, lithium aluminum hydride in the presence of a solvent such as ether, tetrahydrofuran or the like or sodium borohydride in the presence of a solvent such as methanol, ethanol or the like, at room temperature or at the reflux temperature of the solvent.

In reaction step (b), a compound of formula VI is converted to a compound of formula Id by alkylation utilizing a Grignard reagent or an organolithium reagent. More particularly, a compound of formula VI is treated with a Grignard reagent such as an alkylmagnesium halide in a solvent such as diethyl ether or dibutyl or diisopentyl ether at room temperature or at the reflux temperature of the solvent. Alternatively, a compound of formula VI is treated with an organolithium reagents. For example, a compound of formula VI is treated with methyllithium under the conditions set out above for the Grignard reaction and under an atmosphere of nitrogen.

The compounds of formula I above form pharmaceutically acceptable acid addition salts with inorganic acids. Thus, the compounds of the present invention form pharmaceutically acceptable acid addition salts with inorganic acids such as hydrochloric acid, hydrobromic acid, sulfuric acid and phosphoric acid, and with organic acids such as tartaric acid, oxalic acid, citric acid, camphorsulfonic acid, ethanesulfonic acid, toluenesulfonic acid, salicyclic acid, ascorbic acid, maleic acid, succinic acid, formic acid, acetic acid and the like.

The compounds of formula I and their pharmaceutically acceptable salts are useful as analgesics agents. These compounds, when administered orally or parentally, provide a relief from pain in the same manner as codeine.

The compounds of formula I and salts as herein described can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The daily dose administered of a compound of formula I will of course vary with the particular compounds employed because of the very potency of the compound the chosen route of administration and the size of the recipient. The dosage administered is not subject to definite bounds but it will usually be in effective amounts of the pharmacological function of a compound formula I. Representative of a typical method for administering the compounds of formula I is by the oral administration route. By this route, a tablet containing a compound of formula I can be administered orally at the rate of 0.01 microgram to 0.15 microgram per day per kilogram of body weight.

As stated above, the compounds of formula I above and their salts are used as analgesic pain killing agents. This analgesic activity can be demonstrated in the standard phenylquinone writhing test (Sigmund et al., Proc. Soc. Exp. Biol. Med. 95:729 [1957]). The compounds of formula I of the invention significantly reduce pain and produce analgesic effects in mice exposed to intraabdominally induced chemical pain. The $ED_{50}$ was the dose which reduced the total number of writhes by 50%. The analgesic activity can also be demonstrated in the tail flick test. A modification of the tail flick test described by Dewey and Harris (in: S. Ehrenpreis and A. Neidle (eds.), Methods in Narcotics Research, Marcel Dekker, Inc., New York, 1975, pp. 101–108) was used to measure the tail flick reaction times following oral or subcutaneous administration of the compounds of formula I of the invention.

More specifically, groups of 10 male mice (Charles River, CF-1/CD, 18–22 gm) were placed in individual stainless steel, ventilated, cylindrical restrainers with their tails protruding through a hole at one end. The restraining tubes were positioned on a sliding platform so that each mouse, in turn, could be exposed to a high intensity lamp. The rays from the lamp were focused by means of a parabolic reflector directly on the tail. The intensity of the heat was adjusted by means of a rheostat so that untreated mice would responsed in approximately 2 to 4 seconds. When the endpoint response occurred (a sudden twitch of the tail, removing it from the path of the radiant heat stimulus), the experimenter stopped a reaction time clock. In the event that no response occurred within 10 seconds (the cutoff time), the tester terminated the trial and assigned a latency score of 10 seconds for that trial. The reaction time of each mouse was determined before and again 30,60,90 and 120 minutes after treatment.

Each group of 10 mice was treated orally or subcutaneously with vehicle (normal saline) or with logarithmically spaced doses of the test compounds. For most compounds, four dose levels, which were studied in a single test session, were sufficient to provide a satisfactory estimate of the ED50. Occasionally, five or six doses levels were needed. In some of these cases, the data for a given compound were collected in two test sessions and the results were combined for analysis. Because of this, some vehicle control groups and dosed groups consisted of a total of 20 mice, rather than 10.

Doses were calculated as the salts of all the compounds. Injection volume was 0.1 ml/10 g body weight. For each test compound, ED 50 values were calculated separately for each test. Log dose regression analysis and Fieller's Theorem were used to compute the ED 50 and its 95 percent confidence limits. The analysis was performed on the tail flick latency scores of all mice that were treated with a test compound. For any given test, the average tail flick latency score of the vehicle control group was calculated and a latency value, Z, was derived from this, as follows:

$$Z = \frac{\text{cutoff time} - \text{mean vehicle control latency}}{2},$$

where the cutoff time was 10 seconds. Thus, Z represented 50 percent of the maximum possible response that could have been attained, based upon the performance of the vehicle control group. The value of Z was entered as an interpolate into the regression analysis so that an $ED_{50}$, defined as the dose that increased tail flick latencies by 50 percent of the maximum possible response, could be computed.

When the following compounds of formula I are utilized as the test substances, analgesic activity is observed as shown by the following $ED_{50}$ levels when compared to the standard analgesic agent morphine:

TABLE I
SUMMARY - MOUSE ANALGESIC TESTS

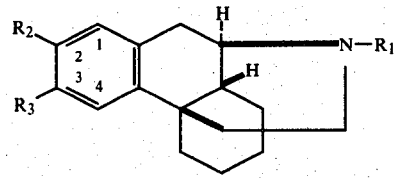

| | | | | ED50 (mg/kg) | | | |
| | | | | Writhing | | Tail Flick | |
| Compound | $R_3$ | $R_2$ | $R_1$ | Oral | Subcu. | Oral | Subcu. |
|---|---|---|---|---|---|---|---|
| Morphine Sulfate | | | | 2.2 | 0.26 | 26.8 | 6.0 |
| (—)-3-Acetyl-N—methylmorphinan D-tartrate | CH$_3$CO | H | CH$_3$ | 0.50 | 0.08 | 2.0 | 3.9 |
| (—)-1-[N—(Cyclopropylmethyl)morphinan-3-yl]ethanone hydrochloride | CH$_3$CO | H | CH$_2$—◁ | 2.1 | 0.18 | 1.5 | 2.3 |
| (—)-2-Acetyl-N—methylmorphinan D-tartrate | H | COCH$_3$ | CH$_3$ | 22.3 | 4.0 | 75.0 | >50 |
| (—)-α-17-Dimethylmorphinan-3-methanol hydrochloride | CH$_3$CH(OH) | H | CH$_3$ | 0.36 | 0.24 | 1.1 | 1.3 |
| (—)-α, α-17-Trimethylmorphinan-3-methanol hydrochloride | (CH$_3$)$_2$C(OH) | H | CH$_3$ | 2.5 | 1.05 | 12.0 | 4.3 |
| (—)-3-Acetyl-17-morphinanpropanenitrile hydrochloride | CH$_3$CO | H | CH$_2$CH$_2$CN | 4.4 | 0.57 | 51.2 | 6.1 |
| (—)-1-[N—(2-Phenethyl)morphinan-3-yl]ethanone D-tartrate hemihydrate | CH$_3$CO | H | CH$_2$CH$_2$—⌬ | 1.2 | 0.39 | 10.4 | 1.8 |
| (—)-1-(17-Methylmorphinan-3-yl)-1-propanone hydrochloride | CH$_3$CH$_2$CO | H | CH$_3$ | 1.9 | 0.22 | 12.0 | 2.3 |
| (—)-3-Acetyl-N—cyclobutylmethylmorphinan hydrochloride | CH$_3$CO | H | CH$_2$—◇ | 5.7 | 1.2 | 27.6 | 4.9 |
| (—)-1-[17-(3-Methyl-2-butenyl)morphinan-3-yl]ethanone d-tartrate monohydrate | CH$_3$CO | H | CH$_2$CH=C(CH$_3$)$_2$ | 43.0 | 5.9 | 115.4 | ~50 |
| (—)-(17-Methylmorphinan-3-yl)-phenylmethanone d-tartrate | C$_6$H$_5$CO | H | CH$_3$ | 35.5 | 22.2 | >200 | >50 |

The Examples which follow further illustrate the invention. All temperatures are in degrees Centigrade unless otherwise mentioned.

EXAMPLE 1

Preparation of (—)-3- and 2-Acetyl-N-methylmorphinan

Under nitrogen 44.0 g of aluminum chloride (anhydrous) was added to 450 ml of 1,2-dichloroethane at ice-bath temperature. To the rapidly stirred mixture, 37.0 g of (—)-N-methylmorphinan hydrochloride was added portionwise over a period of 15 minutes maintained at ice-bath temperature. The reaction mixture was stirred for an additional 15 minutes at the same temperature and a solution of 20.12 g of freshly distilled acetyl chloride in 15 ml of 1,2-dichloroethane was added dropwise. After the addition was completed, the cooling bath was removed, and the mixture was allowed to warm up to room temperature. After heating at reflux for 3 hrs, it was cooled and poured on 800 ml ice-water. The aqueous suspension was made basic with 10 N sodium hydroxide and extracted with chloroform (2×1 L). The combined extracts were washed with water (1 L) and dried over magnesium sulfate. Removal of the solvent gave 26.9 g (71%) of a crude mixture of (—)-3- and 2-acetyl-N-methylmorphinan.

EXAMPLE 2

(—)-3-Acetyl-N-methylmorphinan d-Tartrate

A hot solution of 63.4 g of a mixture of (—)-3- and 2-acetyl-N-methylmorphinan in 238 ml of ethanol was combined with a hot solution of 34.0 g of d-tartaric acid in 238 ml of ethanol. The clear solution was seeded with a few crystals of (—)-3-acetyl-N-methylmorphinan d-tartrate and allowed to crystallize at room temperature for 24 hours. The crystals were then collected by filtration, washed with ethanol and recrystallization from hot ethanol (a total volume of 600 ml at room temperature for 24 hours) afforded 34.6 g (36%) of pure (—)-3-acetyl-N-methylmorphinan d-tartrate, mp 179°–181°, $[\alpha]^{25}D$-6.10° (c 1.17, MeOH).

Analysis: $C_{19}H_{25}NO \cdot C_4H_6O_6$ (433.5): Calcd: C, 63.73; H, 7.21; N, 3.23. Found: C, 63.44; H, 7.39; N, 3.14.

EXAMPLE 3

Preparation of (—)-3-Acetyl-N-methylmorphinan (—)-3-Acetyl-N-methylmorphinan d-tartrate, 4.30 g was suspended in 20 ml water and made basic with concentrated ammonium hydroxide. The resulting suspension was extracted with ether (2×40 ml). The ether extracts were washed with water and dried over magnesium sulfate. Removal of the solvent gave 2.8 g (99%) of (—)-3-acetyl-N-methylmorphinan. For analysis, a sample of this compound was distilled, bp 175°–185° (0.2 mm), $[\alpha]^{25}D$-47.14° (c 1.17, MeOH).

Analysis: $C_{19}H_{25}NO \cdot (283.4)$: Calcd: C, 80.52; H, 8.89; N, 4.94. Found: C, 80.75; H, 8.96; N, 4.81.

The perchlorate salt of the above (—)-3-acetyl-N-methylmorphinan was prepared in ethanol, with perchloric acid (70%) and recrystallized from ethanol, mp 226°–228°, $[\alpha]^{25}D$-20.64° (c 1.01, meOH).

Analysis: $C_{19}H_{25}NO \cdot HClO_4$: (383.84) Calcd: C, 59.45; H, 6.83; N, 3.65. Found: C, 59.53; H, 6.81; N, 3.91.

EXAMPLE 4

Preparation of (—)-2-Acetyl-N-methylmorphinan d-Tartrate

The filtrates obtained in the separation of (—)-3-acetyl-N-methylmorphinan d-tartrate were concentrated to a volume of about 400 ml, then warmed on the steam-bath until clear solution was obtained. The solution was seeded with a few crystals of (—)-2-acetyl-N-methylmorphinan d-tartrate and allowed to crystallize at room temperature for 7 days. The crystals were separated by filtration, washed with ethanol and recrystallized from hot ethanol (2B) a total volume of 450 ml at room temperature over a period of 7 days. The crystals were collected by filtration, washed with ethanol and dried, thus affording 18.0 g (19%) of crude (—)-base d-tartrate mp 168°–170°. A third and final recrystallization from ethanol (2B), a total volume of 300 ml at room temperature and after 21 days yielded 16.3 g (17%) of pure (—)-2-acetyl-N-methylmorphinan d-tartrate, mp 188°–190°, $[\alpha]^{25}D$-4.90° (c 1.01, meOH).

Analysis: $C_{19}H_{25}NO \cdot C_4H_6O_6$: (433.5) Calcd: C, 63.73; H, 7.21; N, 3.23. Found: C, 63.51; H, 7.16; N, 3.35.

EXAMPLE 5

Preparation of (—)-2-Acetyl-N-methylmorphinan (—)-2-Acetyl-N-methylmorphinan d-tartrate 0.25 g was suspended in water and made basic with concentrated ammonium hydroxide. The resulting suspension was extracted with ether. The combined ether extracts were washed with water and dried over magnesium sulfate. Removal of the solvent gave the crude (—)-2-acetyl-N-methylmorphinan. For analysis, this compound was distilled, bp 175°–180° (0.1 mm), $[\alpha]^{25}D$-55.67° (c 1.04, MeOH).

Analysis: $C_{19}H_{25}NO$: (283.4) Calcd: C, 80.52; H, 8.89; N, 4.94. Found: C, 80.65; H, 9.03; N, 4.92.

EXAMPLE 6

Preparation of (—)-3-Acetylmorphinan-17-carboxylic Acid (Trichloroethyl) ester

To a mixture of 2.7 g of (—)-3-acetyl-N-methylmorphinan, 50 ml of benzene and 20 mg of potassium carbonate, was added dropwise 2.11 g of 2,2,2-trichloroethyl chloroformate in 10 ml of benzene. The reaction mixture was stirred at reflux temperature for 48 hours and after cooling it was diluted with 100 ml ether. The ether solution was extracted with 1 N hydrochloric acid (2×30 ml) and dried over magnesium sulfate. Removal of the solvent gave 2.8 g (66%) of crude (—)-3-acetylmorphinan-17-carboxylic acid (trichloroethyl)ester. For analysis, a sample of this compound was distilled, bp 230°–240° (0.1 mm), $[\alpha]^{25}D$-127.21° (c 1.11, MeOH).

Analysis: $C_{21}H_{24}Cl_3NO_3$: (444.77) Calcd: C, 56.71; H, 5.44; N, 3.15. Found: C, 56.79; H, 5.48; N, 2.93.

EXAMPLE 7

(—)-1-(Morphinan-3-yl)ethanone

To a solution of 2.4 g of (—)-3-acetylmorphinan-17-carboxylic acid (trichloroethyl)ester in 40 ml of 90% acetic acid was added portionwise, 2.5 g of zinc-dust. The mixture was stirred at room temperature for 16 hours and filtered. The filtrate was concentrated in vacuo and the residue was partitioned between 40 ml ether and dilute ammonium hydroxide. The ether solution was extracted with 60 ml of 4 N hydrochloric acid. The acidic solution was basified with concentrated ammonium hydroxide and extracted with ether (2×30 ml). The ether solution was dried over magnesium sulfate and removal of the solvent gave 1.0 g (71%) of crude (—)-1-(morphinan-3-yl)ethanone. For analysis, a sample of this compound was distilled, bp 165°–175° (0.1 mm), $[\alpha]^{25}D$-24.77° (c 1.06, MeOH).

Analysis: $C_{18}H_{23}NO$: (269.36) Calcd: C, 80.26; H, 8.61; N, 5.20. Found: C, 80.53; H, 8.59; N, 5.21.

EXAMPLE 8

Preparation of
(−)-1-[N-(Cyclopropylmethyl)morphinan-3-yl]ethanone

To a mixture of 0.8 g of (−)-1-(morphinan-3-yl)-ethanone, 0.6 g of sodium bicarbonate and 10 ml dimethylformamide, was added 0.3 g of cyclopropylmethyl chloride. After the mixture had been heated at reflux for 18 hours, it was cooled to room temperature and filtered. The filtrate was concentrated under reduced pressure and the residue was dissolved in 60 ml ether. The ether solution was washed with water, dried over magnesium sulfate and removal of the solvent gave 0.8 g (83%) of crude (−)-1-[N-(cyclopropylmethyl)morphinan-3-yl]ethanone. For analysis, a sample of this compound was distilled, bp 185°–195° (0.1 mm), $[\alpha]^{25}$ D-83.21° (c 1.02, MeOH).

Analysis: $C_{22}H_{29}NO$: (323.45) Calcd: C, 81.69; H, 9.04; N, 4.33. Found: C, 81.37; H, 8.90; N, 4.20.

The above base, 0.69 g, on treatment with hydrogen chloride (anhydrous) in ethyl acetate, gave the crude hydrochloride, which after crystallization from acetone-ether afforded 0.7 g (91%) of (−)-1-[N-(cyclopropylmethyl)morphinan-3-yl]-ethanone hydrochloride, mp 263°–265°, $[\alpha]^{25}$ D-57.25° (c 0.98, MeOH).

Analysis: $C_{22}H_{29}NO \cdot HCl$: (359.91) Calcd: C, 73.41; H, 8.40; N, 3.89. Found: C, 73.04; H, 8.27; N, 4.06.

EXAMPLE 9

Preparation of
(−)-3-Acetyl-N-cyclobutylmethylmorphinan

To a mixture of 1.7 g, (−)-1-(morphinan-3-yl)ethanone, 1.5 g of potassium carbonate and 40 ml dimethylformamide, was added 1.2 g of cyclobutylmethyl chloride. After the mixture had been heated at 100°–110° for 16 hours it was cooled to room temperature and filtered. The filtrate was concentrated under reduced pressure and the residue was dissolved in 120 ml of ether. The ether solution was washed with water (2×20 ml), dried over magnesium sulfate and removal of the solvent gave 1.6 g (76%) of crude (−)-3-acetyl-N-cyclobutylmethylmorphinan. For analysis, a sample of this compound was distilled, bp 200°–210° (0.05 mm), $[\alpha]^{25}$ D-80.64° (c 1.03, MeOH).

Analysis: $C_{23}H_{31}NO$: (337.47) Calcd: C, 81.85; H, 9.26; N, 4.15. Found: C, 81.75; H, 9.10; N, 4.33.

The crude base, 1.3 g, on treatment with hydrogen chloride (anhydrous) in ethyl acetate, gave the crude hydrochloride, which after crystallization from ethanol-ether afforded 0.186 g (13%) of (−)-3-acetyl-N-cyclobutylmethylmorphinan hydrochloride, mp 220°–222°, $[\alpha]^{25}$ D-54.43° (c 0.81, MeOH).

Analysis: $C_{23}H_{31}NO \cdot HCl$: (373.97) Calcd: C, 73.87; H, 8.63; N, 3.75. Found: C, 73.54; H, 8.46; N, 3.82.

EXAMPLE 10

Preparation of
(−)-1-[N-(2-Phenethyl)morphinan-3-yl]ethanone

A mixture of 1.5 g of (−)-1-(morphinan-3-yl)ethanone, 1.3 g (2-bromoethyl)benzene and 1.1 g of potassium carbonate (anhydrous) in 40 ml dimethylformamide was heated under nitrogen at 110° for 16 hours. After cooling, the reaction mixture was filtered and the filtrate was concentrated under reduced pressure. The residue was dissolved in ether and the ether solution was washed with water and dried over magnesium sulfate. Removal of the solvent gave 1.8 g (85%) of crude (−)-1-[N-(2-phenethyl)morphinan-3-yl]ethanone. For analysis, a sample of this compound was distilled, bp 210°–220° (0.05 mm), $[\alpha]^{25}$ D-100.72° (c 1.08, MeOH).

Analysis: $C_{26}H_{31}NO$: (373.50) Calcd: C, 83.60; H, 8.37; N, 3.75. Found: C, 83.42; H, 8.16; N, 3.88.

The above base, 1.7 g, was dissolved in 3 ml of hot ethanol and combined with a hot solution of 0.72 g of d-tartaric acid in 4 ml of ethanol. The mixture was allowed to crystallize at room temperature for 2 hours and the crystals were separated by filtration to give 2.2 g (92%) of (−)-1-[N-(2-phenethyl)morphinan-3-yl]ethanone d-tartrate hemihydrate, mp 100°–102° (d), $[\alpha]^{25}$ D-45.69° (c 1.08, MeOH).

Analysis: $C_{26}H_{31}NO \cdot C_4H_6O_6$ 0.5 $H_2O$: (532.60) Calcd: C, 67.64; H, 7.19; N, 2.62. Found: C, 68.00; H, 7.50; N, 3.05.

EXAMPLE 11

Preparation of
(−)-3-Acetyl-17-morphinanpropanenitrile

To a mixture of 1.5 g of (−)-1-(morphinan-3-yl)ethanone, 2.3 g of triethylamine and 35 ml of absolute ethanol, was added 0.35 g of acrylonitrile. After the mixture had been heated at reflux for 16 hours the solvent and excess of reagents were removed under reduced pressure to give 1.7 g (94%) of crude (−)-3-acetyl-17-morphinanpropanenitrile. For analysis, a sample of this compound was distilled, bp 220°–230° (0.05 mm), $[\alpha]^{25}$ D-65.5° (c 1.03, MeOH).

Analysis: $C_{21}H_{26}N_2O$ (322.42): Calcd: C, 78.22; H, 8.13; N, 8.69. Found: C, 78.13; H, 8.16; N, 8.47.

The above base, 1.6 g, on treatment with hydrogen chloride (anhydrous) in ethyl acetate, afforded the crude hydrochloride, which after recrystallization from ethanolether gave 1.6 g (94%) of (−)-3-acetyl-17-morphinanpropanenitrile hydrochloride mp 245°–247° (d), $[\alpha]^{25}$ D-54.93° (c 0.94, MeOH).

Analysis: $C_{21}H_{26}N_2O$ HCl (358.87): Calcd: C, 70.28; H, 7.58; N, 7.81. Found: C, 70.26; H, 7.61; N, 7.82.

EXAMPLE 12

Preparation of
(−)-3-Acetyl-N-[(2-furylmethyl)carbonyl]morphinan

To a mixture of 1.5 g, (−)-1-(morphinan-3-yl)ethanone, 1.7 g of triethylamine and 15 ml of methylene chloride at ice-bath temperature was added a solution of 1.3 g of 2-furyl acetyl chloride in 10 ml of methylene chloride over a period of 1 hour. After the mixture had been refluxed for 4 hours, it was cooled to room temperature and the solvent was removed under reduced pressure. The residue was dissolved in 100 ml ether and the ether solution was washed with 1 N hydrochloric acid (2×15 ml) then with water and dried over magnesium sulfate. Removal of the solvent gave 1.9 g (90%) of crude (−)-3-acetyl-N-[(2-furylmethyl)carbonyl]morphinan. For analysis, a sample of this compound was distilled, bp 235°–245° (0.05 mm), $[\alpha]^{25}$ D-160.43° (c 0.94, MeOH).

Analysis: $C_{24}H_{27}NO_3$: (377.45) Calcd: C, 76.36; H, 7.21; N, 3.71. Found: C, 76.18; H, 7.10; N, 3.83.

EXAMPLE 13

Preparation of (−)-3-Acetyl-N-furylethylmorphinan

A mixture of 1.2 g of (−)-3-acetyl-N-[(2-furylmethyl)carbonyl]morphinan, ethylene glycol (0.5 g) and 20 ml of benzene containing a catalytic amount of p-toluenesulfonic acid was heated at reflux for 20 hours with removal of the water by means of a Dean-Stark apparatus. After cooling, the solution was washed with 20 ml of 1 N sodium hydroxide, then with water (2×20 ml) and dried over magnesium sulfate. Removal of the solvent under reduced pressure gave 1.1 g (84%) of the ketal derivative, which was used in subsequent steps without purification. To a suspension of 55 mg of lithium aluminum hydride in 8 ml of tetrahydrofuran, 0.5 g of the ketal derivatives in 6 ml of tetrahydrofuran was added dropwise. After the mixture had been refluxed overnight, it was cooled to room temperature and 5 ml of ethyl acetate followed by 2 ml of water were added dropwise. The organic phase was separated and the solvent was removed under reduced pressure. The residue was partitioned between 25 ml of 1 N hydrochloric acid and 25 ml of ether. The acidic solution was made basic with concentrated ammonium hydroxide and extracted with ether (2×25 ml). The combined ether solutions were washed with water (2×20 ml), dried over magnesium sulfate and removal of the solvent gave 0.21 g (49%) of crude (−)-3-acetyl-N-furylethylmorphinan. This compound was chromatographed over 50 g silica gel using 6% methanol in methylene chloride as eluates to give 0.16 g (37%) of pure (−)-3-acetyl-N-furylethylmorphinan, bp 185°–190° (0.06 mm), [α] D-97.91° (c 0.91, MeOH).

Analysis: $C_{24}H_{29}NO_2$: (363.5) Calcd: C, 79.30; H, 8.04; N, 3.85. Found: C, 79.09; H, 8.01; N, 4.01.

The above base, 0.16 g, on treatment with hydrogen chloride (anhydrous) in ethyl acetate, gave the crude hydrochloride, which after recrystallization from acetonitrileether gave pure (−)-3-acetyl-N-furylethylmorphinan hydrochloride, mp 205°–207°, $[α]^{25}$ D-67.45° (c 0.85, MeOH).

Analysis: $C_{24}H_{29}NO_2.HCl$: (399.96) Calcd: C, 72.07; H, 7.56; N, 3.50. Found: C, 72.19; H, 7.56; N, 3.80.

EXAMPLE 14

Preparation of (−)-α-17-Dimethylmorphinan-3-methanol

To a stirred solution of 3.0 g of (−)-3-acetyl-N-methylmorphinan in 50 ml methanol, 3.0 g of sodium borohydride was added portionwise and the mixture was stirred at room temperature for 16 hours. The solvent was removed under reduced pressure and the residue was partitioned between 50 ml water and 100 ml ether. The ether solution was washed with water, dried over magnesium sulfate and removal of the solvent gave 2.8 g (93%) of an epimeric mixture of crude (−)-α-17-dimethylmorphinan-3-methanol. For analysis, a sample of this compound was distilled, bp 170°–180° (0.05 mm), $[α]^{25}$ D-41.06° (c 1.07, MeOH).

Analysis: $C_{19}H_{27}NO$: (285.40) Calcd: C, 79.95; H, 9.54; N, 4.91. Found: C, 79.98; H, 9.50; N, 4.75.

The crude base, 2.8 g, on treatment with hydrogen chloride (anhydrous) in ethyl acetate, afforded the crude hydrochloride, which after crystallization from ethanol-ether gave 2.5 g (79%) of pure (−)-α-17-dimethylmorphinan-3-methanol hydrochloride, mp 219°–221°, $[α]^{25}$ D-30.0° (c 1.04, MeOH).

Analysis: $C_{19}H_{27}NO.HCl$: (321.89) Calcd: C, 70.90; H, 8.77; N, 4.35. Found: C, 70.39; H, 9.08; N, 4.16.

EXAMPLE 15

Preparation of (−)-α,α-17-Trimethylmorphinan-3-methanol

Under nitrogen, 2.0 g of (−)-3-acetyl-N-methylmorphinan was dissolved in 100 ml ether. The stirred solution was cooled in an ice-bath while 17.0 ml of methyllithium (1.3 M in ether) was added dropwise over a period of 20 minutes. The reaction mixture was allowed to warm up to room temperature and stirred at this temperature for an additional 20 minutes. The mixture was poured on ice-water and the ether phase was separated. The aqueous solution was extracted with ether (2×50 ml) and the combined ethereal extracts were washed with water then dried over magnesium sulfate. Removal of the solvent gave 1.7 g (81%) of (−)-α,α-17-trimethylmorphinan-3-methanol. For analysis, a sample of this compound was distilled, bp 175°–180° (0.05 mm), $[α]^{25}$ D-38.6° (c 1.09, MeOH).

Analysis: $C_{20}H_{29}NO$: (299.43) Calcd: C, 80.22; H, 9.76; N, 4.68. Found: C, 80.05; H, 9.56; N, 4.54.

The crude base, 1.7 g, on treatment with hydrogen chloride (anhydrous), in ethyl acetate, gave the crude hydrochloride, which after recrystallization from acetone afforded 1.9 g (99%) of pure (−)-α,α-17-trimethylmorphinan-3-methanol hydrochloride, mp 206°–208°, $[α]^{25}$ D-21.95° (c 0.97, MeOH).

Analysis: $C_{20}H_{29}NO.HCl$ (335.89) Calcd: C, 71.51; H, 9.00; N, 4.17. Found: C, 70.94; H, 9.00; N, 4.12.

EXAMPLE 16

Preparation of (−)-1-(17-Methylmorphinan-3-yl)-1-propanone

Under nitrogen, 14.2 g of aluminum chloride (anhydrous) was added 140 ml of 1,2-dichloroethane at ice-bath temperature. To the rapidly stirred mixture, 12.0 g of (−)-N-methylmorphinan hydrochloride was added portionwise over a period of 10 minutes. The reaction mixture was stirred for another 15 minutes at the same temperature and then 7.6 g of propionyl chloride in 5 ml of 1,2-dichloroethane was added dropwise. After the addition was completed, the cooling bath was removed, and the mixture was allowed to warm up to room temperature. After heating at reflux for 3 hours, it was cooled and poured on 500 ml of ice-water. The aqueous suspension was made basic with concentrated ammonium hydroxide and extracted with methylene chloride (2×250 ml). The combined extracts were washed with 300 ml of water and dried on magnesium sulfate. Removal of solvent gave 11.8 g (92%) of a crude mixture of (−)-3- and 2-propionyl-N-methylmorphinan.

The above crude mixture, 11.8 g, on treatment with hydrogen chloride (anhydrous) in acetone gave the crude hydrochloride. The crude mixture was dissolved in 40 ml of hot ethanol and allowed to crystallize at room temperature overnight to give 4.7 g (36%) of (−)-1-(17-methylmorphinan-3-yl)-1-propanone hydrochloride, mp 278°–280°, $[α]^{25}$ D-29.51° (c 1.13, MeOH).

Analysis: $C_{20}H_{27}NO.HCl$: (333.87) Calcd: C, 71.94; H, 8.45; N, 4.19. Found: C, 71.78; H, 8.23; N, 4.18.

For analysis, a sample of the free base was prepared from the above hydrochloride, using ammonium hydroxide as base and methylene chloride for extraction. The (−)-1-(17-methylmorphinan-3-yl)-1-propanone was distilled, bp 185°–190° (0.025 mm), $[\alpha]^{25}$ D -47.60° (c 1.05, MeOH).

Analysis: $C_{20}H_{27}NO$: (297.42) Calcd: C, 80.76; H, 9.15; N, 4.71. Found: C, 80.78; H, 8.97; N, 4.70.

EXAMPLE 17

Preparation of (−)-(17-Methylmorphinan-3- and 2-yl)phenylmethanone

Under nitrogen 5.8 g of aluminum chloride (anhydrous) was added to 65 ml of 1,2-dichloroethane (dried over alumina Act. 1) at ice-bath temperature. To the rapidly stirred mixture, 6.2 g of (−)-N-methylmorphinan hydrochloride was added portionwise maintained at ice-bath temperature. The reaction mixture was stirred for an additional 15 minutes and a solution of 6.3 g of benzoyl chloride (distilled) in 10 ml of 1,2-dichloroethane was added dropwise over a period of 40 minutes. After the addition was completed, the cooling bath was removed, and the stirred mixture was allowed to warm up to room temperature. After heating at reflux for 16.5 hours it was cooled and poured on 100 ml ice-water. The aqueous mixture was washed with 100 ml of ether then made basic with 50 ml of 10 N sodium hydroxide and extracted with methylene chloride (3×100 ml). The combined methylene chloride solutions were washed with 100 ml of water and dried over magnesium sulfate. Removal of the solvent gave 6.7 g (87%) of a crude mixture of (−)-(17-methylmorphinan-3- and 2-yl)phenylmethanone.

EXAMINE 18

Preparation of (−)-(17-Methylmorphinan-3-yl)phenylmethanone

A hot solution of 6.7 g of a mixture of (−)-(17-methylmorphinan-3- and 2-yl)phenylmethanone in 75 ml of ethanol was combined with a hot solution of 2.95 g of d-tartaric acid in 25 ml of ethanol. The solution was allowed to crystallize at room temperature for 6 days. The crystals were collected by filtration, washed with ethanol and recrystallized from 50 ml of methanol at room temperature for 6 days affording 2.5 g (26%) of pure (−)-(17-methylmorphinan-3-yl)phenylmethanone d-tartrate, mp 203°–204°, $[\alpha]^{25}$ D-33.36° (c 9.92, MeOH).

Analysis: $C_{24}H_{27}NO \cdot C_4H_6O_6$: (495.57) Calcd: C, 67.86; H, 6.71; N, 2.83. Found: C, 67.98; H, 6.95; N, 2.88.

The above salt, 0.5 g was suspended in water and made basic with 5% sodium hydroxide. The resulting suspension was extracted with methylene chloride. The combined extracts were washed with water and dried over magnesium sulfate. Removal of the solvent gave (−)-(17-methylmorphinan-3-yl)phenylmethanone, which was distilled, bp 220°–230° (0.025 mm), $[\alpha]^{25}$ D-77.07° (c 0.91, MeOH).

A sample of the above base was also crystallized from ether, mp 103°–104°.

Analysis: $C_{24}H_{27}NO$: (345.46) Calcd: C, 83.44; H, 7.88; N, 4.05. Found: C, 83.64; H, 7.84; N, 4.01.

EXAMPLE 19

Preparation of (−)-1-[17-(3-Methyl-2-butenyl)morphinan-3-yl]ethanone

To a mixture of 1.8 g of (−)-1-(morphinan-3-yl)ethanone, 0.6 g of sodium bicarbonate and 25 ml of dimethylformamide, was added 1.0 g of dimethylallyl bromide. After the mixture had been heated at 50° for 16 hours, it was cooled to room temperature and filtered. The filtrate was concentrated under reduced pressure and the residue was partitioned between 50 ml of methylene chloride and 30 ml of water. The methylene chloride solution was washed with water and dried over magnesium sulfate. Removal of the solvent gave 2.1 g (93%) of crude (−)-1-[17-(3-methyl-2-butenyl)morphinan-3-yl]ethanone. For analysis, a sample of this compound was distilled, bp 185°–195° (0.05 mm), $[\alpha]^{25}$ D-76.53° (c 0.98, MeOH).

Analysis: $C_{23}H_{31}NO$: (337.50) Calcd: C, 81.85; H, 9.26; N, 4.15. Found: C, 81.62; H, 9.13; N, 4.29.

The 2.1 g above base was dissolved in hot 7 ml acetone and combined with a hot solution of 0.92 g of d-tartaric acid in acetone. The mixture was allowed to crystallize at room temperature to give the crude tartrate, which after crystallization from isopropanol afforded 1.7 g (55%) of (−)-1-[17-(3-methyl-2-butenyl)-morphinan-3-yl]ethanone d-tartrate monohydrate, mp 105°–110° (d), $[\alpha]^{25}$ D-38.49° (c 0.98, MeOH).

Analysis: $C_{23}H_{31}NO \cdot C_4H_6O_6 \cdot H_2O$: (505.58) Calcd: C, 64.14; H, 7.77; N, 2.77. Found: C, 64.48; H, 7.49; N, 2.70.

EXAMPLE 20

Tablet was formulated as follows:

| Item | Ingredient | mg/tablet |
|---|---|---|
| 1. | (−)-1-[N—(Cyclopropylmethyl)morphinan-3-yl]-ethanone hydrochloride | 5.0 |
| 2. | Lactose | 99.0 |
| 3. | Pregelatinized starch | 10.0 |
| 4. | Corn Starch | 15.0 |
| 5. | Modified Starch | 10.0 |
| 6. | Magnesium stearate | 1.0 |
|  | Weight of tablet | 140 mg |

Procedure

1. Mix items 1,2,3,4 and 5 in a suitable mixer, granulate with water. Dry over night in an oven. Mill through a Fitzpatrick mill.

2. Mix with item 6 and compress on a suitable press.

EXAMPLE 21

A tablet was formulated as follows:

| Item | Ingredient | mg/tablet |
|---|---|---|
| 1. | (−)-1-N—(Cyclopropylmethyl)morphinan-ethanone hydrochloride | 10.0 |
| 2. | Lactose anhydrous | 103.0 |
| 3. | Avicel | 45.0 |
| 4. | Modified starch | 10.0 |
| 5. | Corn starch | 30.0 |
| 6. | Magnesium stearate | 2.0 |
|  | Weight of tablet | 200 mg |

Procedure

1. Mix items 1,2,3,4 and 5 in a suitable mixer for 10 to 15 minutes.

2. Add magnesium stearate (item 6) as a premix and mix for 4 minutes. Compress on a suitable press.

EXAMPLE 22

A capsule Formulation

| Item | Ingredient | mg/capsule |
|---|---|---|
| 1. | (—)-1-N—(Cyclopropylmethyl)morphinan-3-yl-ethanone hydrochloride | 10.0 |
| 2. | Lactose | 218.0 |
| 3. | Corn Starch | 50.0 |
| 4. | Magnesium stearate | 2.0 |
| 5. | Talc | 10.0 |
| | Fill weight of capsule | 290 mg |

Procedure

1. Mix items 1,2 and 3 in a suitable mixer. Mill through suitable mill.
2. Mix with items 4 and 5 and fill on capsule machine.

EXAMPLE 23

A capsule was formulated as follows:

| Item | Ingredient | mg/capsule |
|---|---|---|
| 1. | (—)-3-Acetyl-N—methylmorphinan d-tartarate | 10.0 |
| 2. | Lactose | 218.0 |
| 3. | Corn Starch | 70.0 |
| 4. | Magnesium stearate | 3.0 |
| 5. | Talc | 15.0 |
| | Fill weight of capsule | 370 mg |

Procedure

1. Mix items 1,2 and 3 in a suitable mixer. Mill through suitable mill.
2. Mix with items 4 and 5 and fill on capsule machine.

EXAMPLE 24

A tablet was formulated (Wet Granulation) as follows

| Item | Ingredient | mg/tablet |
|---|---|---|
| 1. | (—)-3-Acetyl-N—methylmorphinan d-tartarate | 0.5 |
| 2. | Lactose | 186.5 |
| 3. | Modified starch | 35 |
| 4. | Pregelatinized starch | 24 |
| 5. | Distilled water qs | — |
| 6. | Magnesium Stearate | 4 |
| | Weight of tablet | 250 mg |

Procedure

1. Mix items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 25

A tablet (Wet granulation) was formulated as follows:

| Item | Ingredient | mg/tablet |
|---|---|---|
| 1. | (—)-1-N—(Cyclopropylmethyl)morphinan-3-yl-ethanone hydrochloride | 2.0 |
| 2. | Lactose | 253.0 |
| 3. | Modified starch | 55 |
| 4. | Pregelatinized starch | 35 |
| 5. | Distilled water qs | — |
| 6. | Magnesium Stearate | 5 |
| | Weight of tablet | 350 mg |

Procedure

1. Mix items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

I claim:

1. A compound of the formula

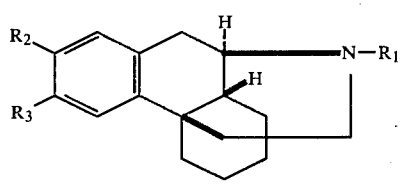

wherein $R_1$ is hydrogen, lower alkyl, lower alkenyl, cycloalkyl-lower alkyl, cyano-lower alkyl, phenyl-lower alkyl, naphthyl-lower alkyl or 5- or 6-membered heterocyclic-lower alkyl selected from the group consisting of thienyl-lower alkyl, pyrrolyl-lower alkyl, furyl-lower alkyl, pyridyl-lower alkyl and pyranyl-lower alkyl, and one of $R_2$ or $R_3$ is hydrogen and the other of $R_2$ or $R_3$ is alkanoyl of 2 to 7 carbon atoms, benzoyl, naphthoyl, trifluoromethylcarbonyl, or

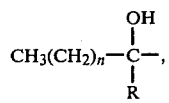

wherein R is hydrogen or lower alkyl and n is 0 to 6, or a salt thereof with a pharmaceutically acceptable acid addition salt.

2. A compound in accordance with claim 1, wherein $R_3$ is hydrogen.

3. A compound in accordance with claim 1, wherein $R_2$ is hydrogen.

4. A compound in accordance with claim 3, wherein $R_3$ is alkanoyl of 2 to 7 carbon atoms.

5. A compound in accordance with claim 4, wherein $R_1$ is cycloalkyl-lower alkyl.

6. A compound in accordance with claim 5, (—)-1-[N-(cyclopropylmethyl)morphinan-3-yl]-ethanone or a salt thereof with a pharmaceutically acceptable acid.

7. A compound in accordance with claim 5, (—)-3-acetyl-N-cyclobutylmethylmorphinan or a salt thereof with a pharmaceutically acceptable acid.

8. A compound in accordance with claim 4, wherein $R_1$ is lower alkyl.

9. A compound in accordance with claim 8, (—)-3-acetyl-N-methylmorphinan or a salt thereof with a pharmaceutically acceptable acid addition salt.

10. A compound in accordance with claim 8, (−)-1-[17-methylmorphinan-3-yl]-1-propane or a salt thereof with a pharmaceutically acceptable acid.

11. A compound in accordance with claim 3, wherein $R_3$ is

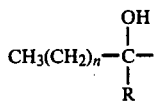

wherein R is hydrogen or lower alkyl and n is 0 to 6.

12. A compound in accordance with claim 11, wherein $R_1$ is lower alkyl.

13. A compound in accordance with claim 12, (−)-α-17-dimethylmorphinan-3-methanol or a salt thereof with a pharmaceutically acceptable acid.

14. A compound in accordance with claim 12, (−)-α,α-17-trimethylmorphinan-3-methanol or a salt thereof with a pharmaceutically acceptable acid.

15. A compound in accordance with claim 1, (−)-1-[17-(3-methyl-2-butenyl)morphinan-3-yl]ethanone.

16. A compound in accordance with claim 1, (−)-(17-methylmorphinan-3-yl)phenylmethanone.

17. A compound in accordance with claim 1, (−)-1-[N-(2-phenethyl)morphinan-3-yl]ethanone.

18. A compound in accordance with claim 1, (−)-3-acetyl-17-morphinanpropanenitrile.

19. A compound in accordance with claim 1, (−)-2-acetyl-N-methylmorphinan.

20. A pharmaceutical composition comprising an analgesically effective amount of a compound of the formula

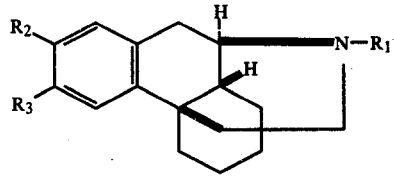

wherein $R_1$ is hydrogen, lower alkyl, lower alkenyl, cycloalkyl-lower alkyl, cyano-lower alkyl, phenyl-lower alkyl, naphthyl-lower alkyl or 5- or 6-membered heterocyclic-lower alkyl selected from the group consisting of thienyl-lower alkyl, pyrrolyl-lower alkyl, furyl-lower alkyl, pyridyl-lower alkyl and pyranyl-lower alkyl, and one of $R_2$ or $R_3$ is alkanoyl of 2 to 7 carbon atoms, benzyl, naphthoyl, trifluoromethylcarbonyl, or

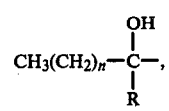

wherein R is hydrogen or lower alkyl and n is 0 to 6, or a salt thereof with a pharmaceutically acceptable acid addition salt, and an inert pharmaceutical carrier.

21. A pharmaceutical composition in accordance with claim 20, wherein the compound of formula I is (−)-1-[N-(cyclopropylmethyl)morphinan-3-yl]-ethanone or a salt thereof with a pharmaceutically acceptable acid addition salt.

22. A pharmaceutical composition in accordance with claim 20, wherein the compound of formula I is (−)-3-acetyl-N-methylmorphinan or a salt thereof with a pharmaceutically acceptable acid addition salt.

* * * * *